United States Patent [19]

Magerlein

[11] 4,212,811

[45] Jul. 15, 1980

[54] BICYCLIC LACTONE INTERMEDIATES

[75] Inventor: Barney J. Magerlein, Kalamazoo, Mich.

[73] Assignee: The Upjohn Company, Kalamazoo, Mich.

[21] Appl. No.: 555,780

[22] Filed: Mar. 6, 1975

Related U.S. Application Data

[60] Continuation of Ser. No. 353,477, Apr. 23, 1973, abandoned, which is a division of Ser. No. 133,842, Apr. 12, 1971, abandoned.

[51] Int. Cl.² ............................................. C07D 307/93
[52] U.S. Cl. ................................................ 260/343.3 P
[58] Field of Search ...................... 260/343.3, 346.2 R, 260/343.3 P

[56] References Cited

U.S. PATENT DOCUMENTS

| | | | |
|---|---|---|---|
| 3,778,450 | 12/1973 | Axen | 260/343.3 |
| 3,901,923 | 8/1975 | Axen | 260/343.3 |

OTHER PUBLICATIONS

Corey et al. *Stereo–Controlled Synthesis of Prostaglandins* $F_{2\alpha}$ and $E_2$ (dl). J.A.C.S. vol. 91, 1969. (pp. 5675–5677 relied on).

*Primary Examiner*—Jose Tovar
*Attorney, Agent, or Firm*—Robert A. Armitage

[57] ABSTRACT

Bicyclic lactone intermediates useful for preparing prostaglandin $E_2$-type, $F_2$-type, $A_2$-type, and $B_2$-type compounds with one or two methyl or ethyl substituents at the C-16 position are disclosed. These prostaglandin-type compounds are useful for the same pharmacological purposes as the corresponding prostaglandins.

15 Claims, No Drawings

BICYCLIC LACTONE INTERMEDIATES

CROSS REFERENCE TO RELATED APPLICATIONS

This application is a continuation of my copending application Ser. No. 353,477, filed Apr. 23, 1973, now abandoned which is a division of my copending application Ser. No. 133,842, filed Apr. 12, 1971, now abandoned.

DESCRIPTION OF THE INVENTION

This invention relates to compositions of matter, and to methods and intermediates for producing them. In particular, the several aspects of this invention relate to novel analogs of some of the known prostaglandins, i.e. prostaglandin $E_1$ ($PGE_1$), prostaglandin $F_1$ ($PGF_{1\alpha}$ and $PGF_{1\beta}$), prostaglandin $A_1$ ($PGA_1$), and prostaglandin $B_1$ ($PGB_1$).

Each of the above-mentioned known prostaglandins is a derivative of prostanoic acid which has the following structure and atom numbering:

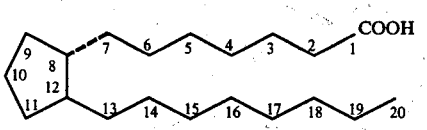

A systematic name for prostanoic acid is 7-[(2β-octyl)-cyclopent-1α-yl]heptanoic acid.

$PGE_1$ has the following structure:

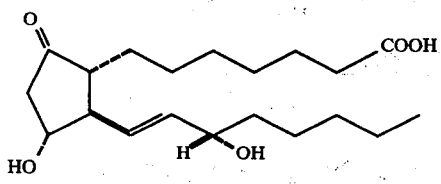

$PGF_{1\alpha}$ has the following structure:

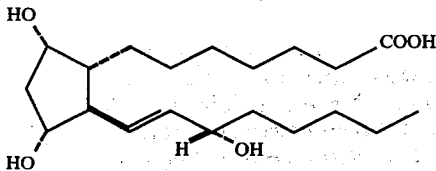

$PGF_{1\beta}$ has the following structure:

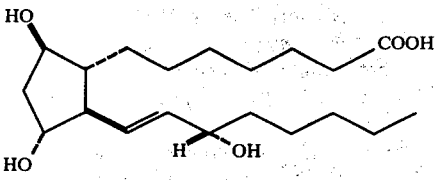

$PGA_1$ has the following structure:

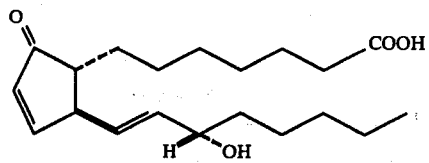

$PGB_1$ has the following structure:

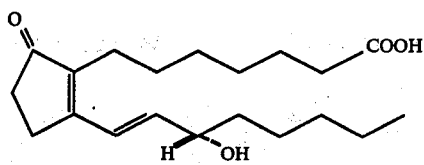

Each of the known prostaglandins $PGE_2$, $PGF_{2\alpha}$, $PGF_{2\beta}$, $PGA_2$, and $PGB_2$ has a structure the same as that shown for the corresponding $PG_1$ compound except that in each, C-5 and C-6 are linked with a cis carbon-carbon double bond. For example, $PGE_2$ has the following structure:

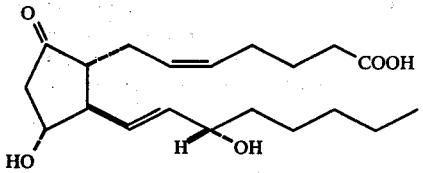

The prostaglandin formulas mentioned above each have several centers of asymmetry. Each formula represents the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., Pharmacol. Rev. 20, 1 (1968), and references cited therein. The mirror image of each formula represents a molecule of the enantiomer of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cyclopentane ring. See, for example, C-8 and C-11 in the $PGE_1$ formula above. Heavy solid line attachments to the cyclopentane ring indicate substituents in beta configuration, i.e., above the plane of the cyclopentane ring. See, for example, C-9 in the $PGF_{1\beta}$ formula above. The side-chain hydroxy at C-15 in the formulas above is in alpha configuration.

Each of the novel prostanoic acid analogs of this invention is encompassed by the following formula or by the combination of that formula and its mirror image:

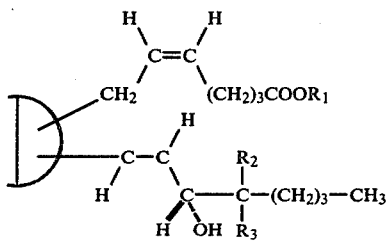

wherein D is one of the four carbocyclic moieties:

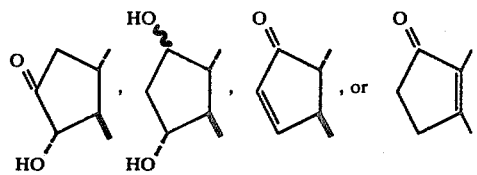

wherein  indicates attachment of hydroxyl to the cyclopentane ring in alpha or beta configuration, wherein $R_1$ is hydrogen, alkyl of one to 8 carbon atoms, inclusive, or a pharmacologically acceptable cation, and wherein $R_2$ and $R_3$ are hydrogen, methyl, or ethyl, provided that at least one of $R_2$ and $R_3$ is not hydrogen.

Formula I, which is written in generic form for convenience, represents $PGE_2$-type compounds when D is

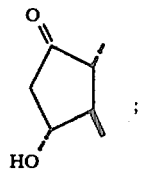

$PGF_{2\alpha}$-type compounds when D is

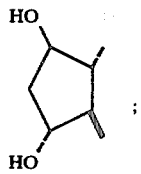

$PGF_{2\beta}$-type compounds when D is

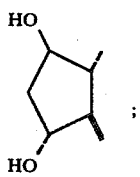

$PGA_2$-type compounds when D is

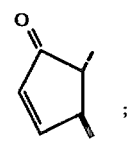

and $PGB_2$-type compounds when D is

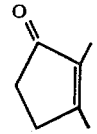

in Formula I, the configuration of the hydroxyl at C-15 is alpha as in the known prostaglandins discussed above. Furthermore, the substituents on the $C_{13}$–$C_{14}$ carbon-carbon double bond are always in trans configuration.

The following formulas represent the novel 16- or 16,16-di-methyl (or -ethyl)-substituted prostaglandin analogs of this invention, wherein $R_1$, $R_2$, and $R_3$ are as defined above.

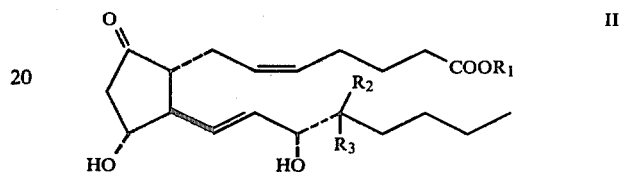

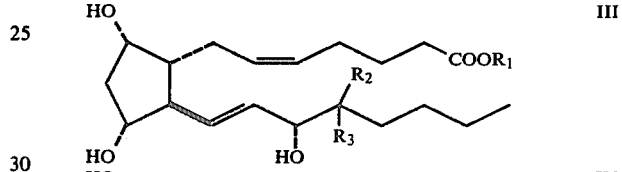

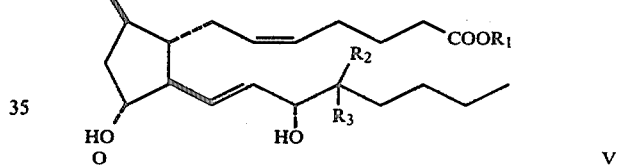

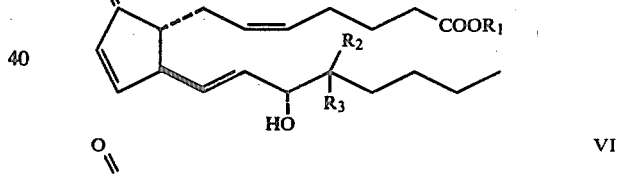

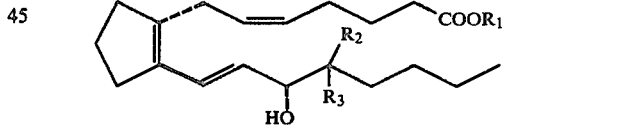

Each of the novel prostanoic acid analogs of this invention has one or two methyl or ethyl substituents at C-16, i.e. the carbon atom adjacent to the hydroxyl-substituted C-15 carbon atom. Thus, these novel prostanoic acid analogs may be conveniently designated 16-methyl-prostaglandins, 16-ethyl-prostaglandins, 16,16-dimethyl-prostaglandins, 16,16-diethyl-prostaglandins, or 16-methyl-16-ethyl-prostaglandins, e.g. 16-methyl-$PGE_2$, 16-ethyl-$PGF_{2\alpha}$, 16,16-dimethyl-$PGF_{2\beta}$, 16,16-diethyl-$PGA_2$, 16-methyl-16-ethyl-$PGB_2$, and the like.

With regard to Formulas I–VI, examples of alkyl of one to 8 carbon atoms, inclusive, are methyl, ethyl, propyl, butyl, pentyl, hexyl, heptyl, octyl, and isomeric forms thereof.

Like the natural prostaglandins described above, these novel 16- or 16,16-di-substituted prostaglandin analogs have several centers of asymmetry. In addition to those found in the natural prostaglandins, there is an asymmetric center at C-16 when that carbon atom is mono-substituted as in the 16-methyl or 16-ethyl PG compounds. 16-Methyl-PGE$_2$, therefore, has two C-16 epimers, both having the same configuration at the other asymmetric centers as that of natural PGE$_2$, i.e. alpha for the side chain at C-8 and alpha for the hydroxyls at C-11 and C-15.

As in the case of the formulas representing the prostaglandins, Formulas I through VI are intended to represent optically active prostanoic acid analogs with the same absolute configuration as PGE$_2$ obtained from mammalian tissues. The novel prostanoic acid derivatives of this invention also include the corresponding racemic compounds. Formula I plus its mirror image are necessary in combination to describe a racemic compound. For convenience hereinafter, when the word "racemic" precedes the name of one of the novel prostanoic acid derivatives of this invention, the intent is to designate a racemic compound represented by the combination of the appropriate Formula I and the mirror image of that formula. When the word "racemic" does not precede the compound name, the intent is to designate an optically active compound represented only by the appropriate Formula I and with the same absolute configuration as PGE$_2$ obtained from animal tissues.

PGE$_1$ and PGE$_2$ and the corresponding PGF$_\alpha$, PGF$_\beta$, PGA, and PGB compounds, and their esters, and pharmacologically acceptable salts, are extremely potent in causing various biological responses. For that reason, these compounds are useful for pharmacological purposes. See, for example, Bergstrom et al., Pharmacol. Rev. 20, 1 (1968), and references cited therein. A few of those biological responses are stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, STP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application. In this application and those following, the lower range of dosage is preferred for humans, the higher range for domestic animals, for example horses or cows.

The PGE and PGA compounds are useful in mammals, including man and certain useful animals, e.g., dogs and pigs, to reduce the control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, $PGF_\alpha$, and $PGF_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during a span of time starting approvimately at the time of ovulation and ending approvimately at the time of menses or just prior to menses. Intravaginal and intrauterine are alternative route of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressing, or as a lotion, cream, or ointment in combination with the usual pharmaceutically acceptable diluents. In some instances, for example, when there is substantial fluid loss as in the case of extensive burns or skin loss due to other causes, systemic administration is advantageous. For example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing one to 500 μg./ml. of the PGB compound or several times that concentration of the PGE compound. Especially for topical use, these prostaglandins are useful in combination with antibiotics, for example, gentamycin, neomycin, polymyxin B, bactiracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel Formula-II 16- and 16,16-di-substituted PGE-type compounds, the novel Formula-III and -IV $PGF_\alpha$ type and $PGF_\beta$-type compounds, the novel Formula-V PGA-type compounds, and the novel Formula-VI PGB-type compounds each cause the biological responses described above for the PGE, $PGF_\alpha$, $PGF_\beta$, PGA, and PGB compounds, respectively, and each of these novel compounds is accordingly useful for the above-described corresponding purposes, and is used for those purposes in the same manner as described above.

The known PGE, $PGF_\alpha$, $PGF_\beta$, PGA, and PGB compounds uniformly cause multiple biological responses even at low doses. For example, PGE₁ and PGE₂ both cause vasodepression and smooth muscle stimulation at the same time they exert antilipolytic activity. Moreover, for many applications, these known prostaglandins have an inconveniently short duration of biological activity. In striking concontrast, the novel prostaglandin analogs of Formulas I to VI are substantially more specific with regard to potency in causing prostaglandin-like biological responses, and have a substantially longer duration of biological activity. Therefore, each of these novel prostaglandin analogs is useful in place of one of the corresponding above-mentioned known prostaglandins for at least one of the pharmacological purposes indicated above for the latter, and is surprisingly and unexpectedly more useful for that purpose because it has a different and narrower spectrum of biological activity than the known prostaglandin, and therefore is more specific in its activity and causes smaller and fewer undesired side effects than the known prostaglandin. Moreover, because of its prolonged activity fewer and smaller doses of the novel prostaglandin analog can frequently be used to attain the desired result.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible selfadministration by the patient.

The 16- and 16,16-di-substituted PGE₂, PGF$_{2\alpha}$, PGF$_{2\beta}$, PGA₂, and PGB₂ type compounds encompassed by Formulas I–VI are used for the purposes described above in the free acid form, in ester form, or in pharmaceutically acceptable salt form. When the ester form is used, the ester is any of those within the above definition of R₁. However, it is preferred that the ester by alkyl of one to four carbon atoms, inclusive. Of those alkyl, methyl and ethyl are especially preferred for optimum absorption of the compound by the body or experimental animal system.

Pharmacologically acceptable salts of these Formula-I-VI compounds useful for the purposes described above are those with pharmaceutically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 atoms, as well as heretocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-meythylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amine-2-methyl-1-propanol, tris(hydroxymethyl)aminomethane, N-phenylethanolamine, N-(p-tertamylphenyl)diethanolamine, galactamine, N-methyl-glucamine, N-methylglycosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the compounds of Formula I-VI are administered in various ways for various purposes, e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility that R₁ in the Formula-I-VI compounds be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparaions such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The 16- and 16,16-di-substituted PGE₂, PGF$_{2\alpha}$, PGF$_{2\beta}$, PGA₂, and PGB₂ type compounds encompassed by Formulas I–VI are produced by the reactions and procedures described and exemplified hereinafter.

The novel 16-alkyl or 16,16-dialkyl PGE₂-type acids and esters of Formula II are prepared by the sequence of transformations shown in Charts A and B wherein Formulas VII through XVIII, and II, includes optically active compounds as shown and racemic compounds of those formulas and the mirror image thereof. Also in Charts A and B, R₂ and R₃ are hydrogen, methyl, or ethyl, provided that at least one of R₂ and R₃ is not hydrogen; R₄ is (1)

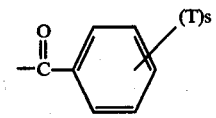

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms; (2)

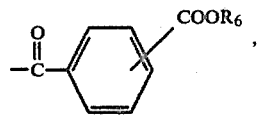

wherein $R_6$ is alkyl of one to 4 carbon atoms, inclusive:
(3)

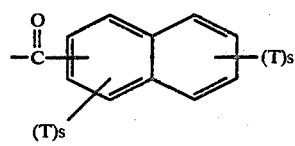

wherein T and s are as defined above; or (4) acetyl; $R_7$ is hydrogen or alkyl of one to 8 carbon atoms, inclusive; THP is tetrahydropyranyl; and ∾ indicates attachment of hydroxyl in alpha or beta configuration. In Chart B the novel $PGE_2$-type compounds of this invention are encompassed by Formula II.

CHART A

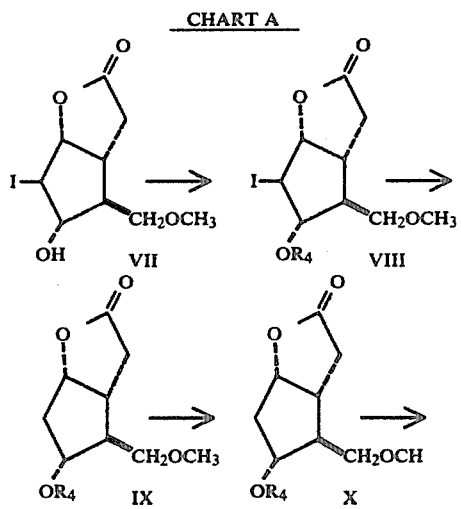

-continued
CHART A

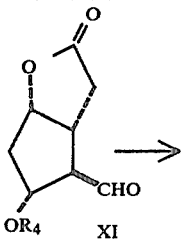

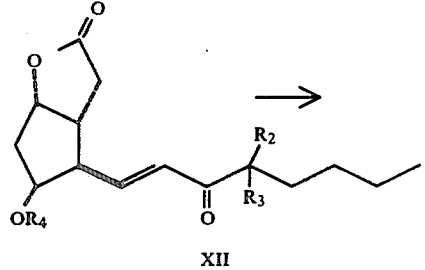

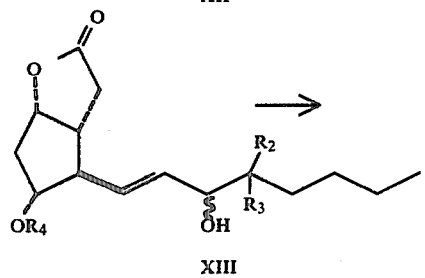

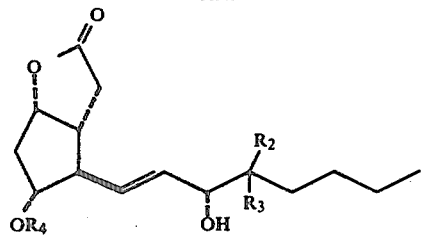

CHART B

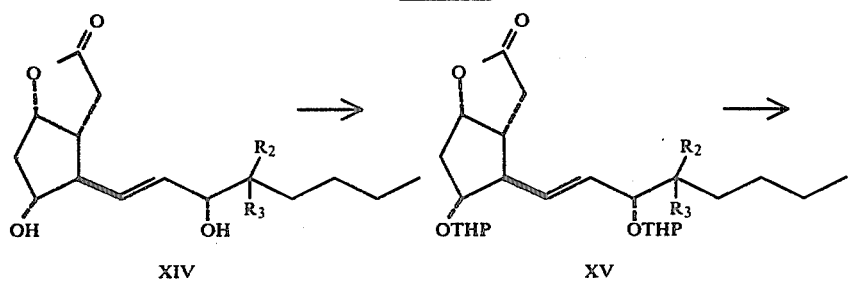

CHART B -continued

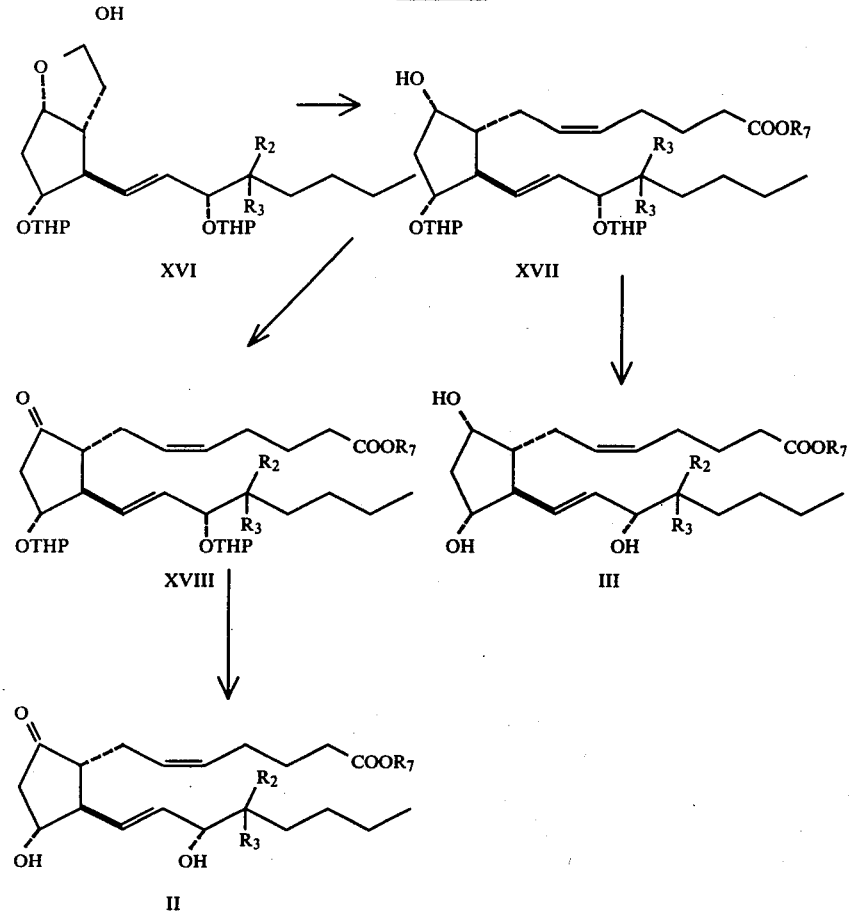

The various PGF$_{2\alpha}$-type and PGF$_{2\beta}$-type compounds encompassed by Formulas III and IV are prepared by carbonyl reduction of the corresponding PGE$_2$-type compounds. For example, carbonyl reduction of 16-methyl-PGE$_2$ gives a mixture of 16-methyl-PGF$_{2\alpha}$ and 16-methyl-PGF$_{2\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium (tri-tert-butoxy)aluminum hydride, the metal borohydrides, especially sodium, potassium and zinc borohydrides, and the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA$_2$-type compounds encompassed by Formula V are prepared by acidic dehydration of the corresponding PGE$_2$ type compounds. For example, acidic dehydration of 16-ethyl-PGE$_2$ gives 16-ethyl-PGA$_2$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Specification 1,097,533. Alkanoic acids of 2 to 6 carbon atoms, inclusive, especially acetic acid, are preferred acids for this acidic dehydration. Dilute aqueous solutions of mineral acids. e.g., hydrochloric acid, especially in the presence of a solubilizing diluent, e.g., tetrahydrofuran, are also useful as reagents for this acidic dehydration, although these reagents may cause partial hydrolysis of an ester reactant.

The various 16-alkyl and 16,16-dialkyl PGB$_2$-type compounds encompassed by Formula VI are prepared by basic dehydration of the corresponding PGE type compounds, or by contacting the corresponding PGA type compounds with base. For example, both 16,16-dimethyl-PGE$_2$ and 16,16-dimethyl-PGA$_2$ give 16,16-dimethyl-PGB$_2$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 mμ for the PGB type compound.

The various transformations of PGE$_2$-type compounds of Formula-II to the corresponding Formula-III PGF$_{2\alpha}$, Formula-IV PGF$_{2\beta}$, Formula-V PGA$_2$, and Formula-VI PGB$_2$ type compounds are shown in Chart C, wherein R$_2$, R$_3$, R$_7$, and    are as defined above.

Reference to Chart A, herein, will make clear the steps for preparing the Formula-VII through -XIII intermediates and thence the Formula-XIV bicyclic lactone diol.

Previously, the preparation of an intermediate bicyclic lactone diol of the formula

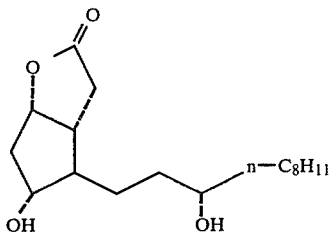

was reported by E. J. Corey et al, J. Am. Chem. Soc. 91, 5675 (1969), and later disclosed in an optically active form by E. J. Corey et al, J. Am. Chem. Soc. 92, 397 (1970). Conversion of this intermediate to PGE$_2$ and PGF$_{2\alpha}$, either in racemic or optically active form, was disclosed in those publications.

The iodolactone of Formula VII in Chart A is known in the art (see Corey et al, above). It is available in either racemic or optically active (+ or −) form. For racemic products, the racemic form is used. For prostaglandins of natural configuration, the laevorotatory form (−) is used.

CHART C

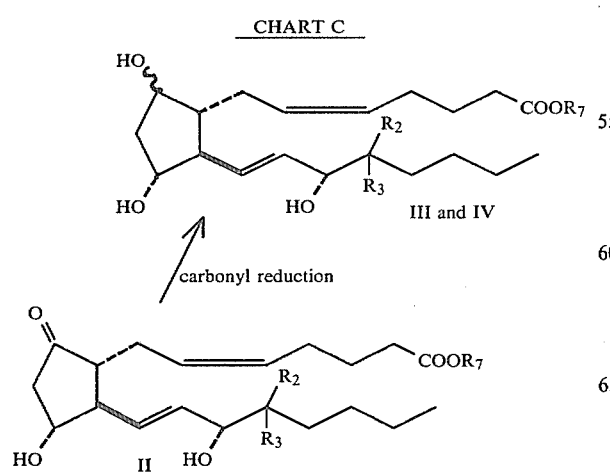

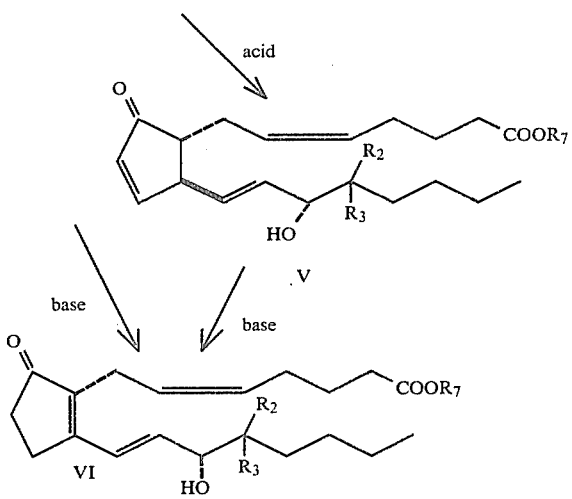

The Formula-VIII compound (Chart A) bears an R$_4$O-moiety at the 4-position, wherein R$_4$ is as defined above. In preparing the Formula-VIII compound by replacing the hydrogen of the hydroxyl group in the 4-position with the acyl group R$_4$, methods known in the art are used. Thus, an aromatic acid of the formula R$_4$OH, wherein R$_4$ is as defined above, for example benzoic acid, is reacted with the Formula-VII compound in the presence of a dehydrating agent, e.g. sulfuric acid, zinc chloride, or phosphoryl chloride; or an anhydride of the aromatic acid of the formula(R$_4$)$_2$O, for example benzoic anhydride, is used.

Preferably, however, an acyl halide, e.g. R$_4$Cl, for example benzoyl chloride, is reacted with the Formula-VII compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°-60° C., contacting the reactants in a liquid medium, e.g. excess pyridine or an inert solvent such as benzene, toluene or chloroform. The acylating agent is used either in stoichiometric amount or in excess.

As examples of R$_4$, the following are available as acids (R$_4$OH), anhydrides ((R$_4$)$_2$O), or acyl chlorides (R$_4$Cl): benzoyl; substituted benzoyl, e.g. (2-, 3- or 4-)-methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, 2-, 3-, or 4-)phenethylbenzoyl, 2-, 3-, or 4-nitrobenzoyl, (2,4- 2,5- or 3,5-)-dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

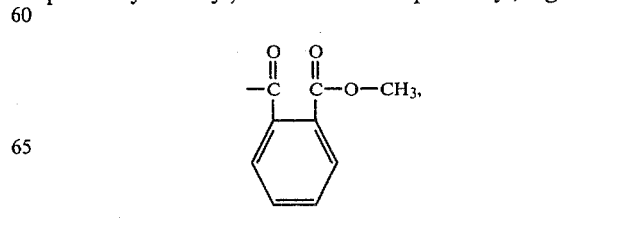

isophthaloyl, e.g.

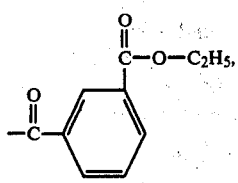

or terephthaloyl, e.g.

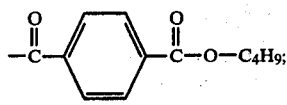

(1- or 2-)naphthoyl; substituted naphthoyl, e.g. (2-, 3-, 4-, 5-, 6-, or 7-)-methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl. There may be employed, therefore, benzoyl chloride, 4-nitrobenzoyl chloride, 3,5-dinitrobenzoyl chloride, and the like, i.e. $R_4Cl$ compounds corresponding to the above $R_4$ groups. If the acyl chloride is not available, it is made from the corresponding acid and phosphorus pentachloride as is known in the art. It is preferred that the $R_4OH$, $(R_4)_2O$, or $R_4Cl$ reactant does not have bulky, hindering substituents, e.g. tert-butyl, on both of the ring carbon atoms adjacent to the carbonyl attaching-site.

The Formula-IX compound is next obtained by deiodination of VIII using a reagent which does not react with the lactone ring or the $OR_4$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis-(2-methylpropionitrile) as initiator.

The Formula-X compound is obtained by demethylation of IX with a reagent that does not attack the $OR_4$ moiety, for example boron tribromide or trichloride. The reaction is carried out preferably in an inert solvent at about 0°-5° C.

The Formula-XI compound is obtained by oxidation of the —$CH_2OH$ of X to —CHO, avoiding decomposition of the lactone ring. Useful for this purpose are dichromatesulfuric acid, Jones reagent, lead tetraacetate, and the like. Especially preferred is Collins' reagent (pyridine-$CrO_3$) at about 0°-10° C.

The Formula-XII compound is obtained by Wittig alkylation of XI, using the sodio derivative of dimethyl 2-oxo-3-methylheptylphosphonate. The trans enone lactone is obtained stereospecifically (see D. H. Wadsworth et al, J. Org. Chem. Vol. 30, p. 680 (1965)).

The Formula-XIII compound is obtained as a mixture of alpha and beta isomers by reduction of XII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane.

For production of natural-configuration PG-type compounds, the desired alpha form of the Formula-XIII compound is separated from the beta isomer by silica gel chromatography.

The Formula-XIV compound is then obtained by deacylation of XIII with an alkali metal carbonate, for example potassium carbonate in methanol at about 25° C.

The transformations of the Formula-XIV compounds to the Formula-II $PGE_2$-type compounds and the Formula-III $PGF_{2\alpha}$-type compounds are shown in Chart B.

The bis(tetrahydropyranyl) ether XV is obtained by reaction of the Formula-XIV diol with dihydropyran in an inert solvent, e.g. dichloromethane, in the presence of an acid condensing agent such as p-toluenesulfonic acid. The dihydropyran is used in excess, preferably 4 to 10 times theory. The reaction is normally complete in 15-30 min. at 20°-30° C.

The lactol XVI is obtained on reduction of the Formula-XV lactone without reducing the 13,14-ethylenic group. For this purpose, diisobutylaluminum hydride is prepared. The reduction is preferably done at $-60°$ to $-70°$ C.

The Formula-XVII compound is obtained by the Wittig reaction, using a Wittig reagent derived from 4-carboxybutyl triphenylphosphonium bromide and sodio dimethylsulfinylcarbanide, together with the Formula-XVI lactol at about 25° C. This Formula-XVII compound serves as an intermediate for preparing either the $PGF_{2\alpha}$-type or the $PGE_2$-type product.

The Formula-III $PGF_{2\alpha}$-type compound is obtained on hydrolysis of the tetrahydropyranyl groups from the Formula-XVII compound, e.g. with methanol/HCl or with acetic acid/water/tetrahydrofuran at 40°-55° C., thereby avoiding formation of $PGA_2$-type compounds as by-products.

To prepare the Formula-II $PGE_2$-type compounds, the bis(tetrahydropyranyl) ether of $PGF_{2\alpha}$ (Formula XVII) is oxidized at the 9-hydroxy position, preferably with Jones reagent. Finally the tetrahydropyranyl groups are replaced with hydrogen, by hydrolysis as in preparing the $PGF_{2\alpha}$-type product.

When the Wittig reagent for preparing the Formula-XVII compound is a carboxylic acid ester, i.e. the phosphonium halide is of the formula $Br(C_6H_5)_3P(CH_2)_4COOR_7$ wherein $R_7$ is alkyl of one to 8 carbon atoms, inclusive, the corresponding ester groups are present in the final $PGF_{2\alpha}$- or $PGE_2$-type products.

As discussed above, the processes of Charts B and C, utilizing the intermediates of Chart A, lead either to acids ($R_7$ is hydrogen) or to alkyl esters ($R_7$ is alkyl of one to 8 carbon atoms, inclusive). When a formula I-VI 16- or 16,16-di-substituted PG-type acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably ethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954).

An alternative method for esterification of the carboxyl moiety of the PG-type compounds comprises transformation of the free acid to the corresponding silver salts, followed by interaction of the salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final Formula I–VI compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the Formula I–VI acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the Formula I–VI acid is dissolved in a suitable solvent of either moderate or low polarity. Examples of the former are ethanol, acetone, and ethyl acetate. Examples of the latter are ethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the Formula I–VI acid with the stoichiometric amount of the corresponding quaternary ammonium hydroxide in water solution, followed by evaporation of the water.

Both optically active and racemic 16- and 16,16-disubstituted PG-type compounds are within the scope of this invention. As disclosed above, racemic intermediates e.g. the racemic Formula-IX aldehyde reacted with racemic Wittig phosphonates lead to racemic products. Optically active intermediates lead to optically active products. Racemic products are separated into optically active products if desired, by resolution using procedures known in the art. For example, a free-acid Formula I–VI compound is resolved by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of Formula I to VI is then obtained by treatment of the salt with an acid by known general procedures.

Those products, racemic or optically active, shown by biological screening tests to have the greatest biological activity are the most useful for the purposes described herein. For example, smooth muscle stimulation is indicated in smooth muscle strip tests (see J. R. Weeks et al., Journal of Applied Physiology, 25, (No. 6), 783 (1968); and antisecretory activity is indicated in in vivo tests with laboratory animals (see A. Robert, "Antisecretory Property of Prostaglandins", Prostaglandin Symposium of the Worcester Foundation for Experimental Biology, Interscience, 1968, pp 47–54).

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer model 421 infrared spectrophotometer. Except when specified otherwise, undiluted (neat) samples are used.

NMR spectra are recorded on a Varian A-60 spectrophotometer in deuterochloroform solutions with tetramethylsilane as an internal standard (downfield).

Mass spectral data are obtained on a Consolidated Electrodynamic Corporation Model 21-110 B High Resolution Mass Spectrometer.

"Brine" as used herein refers to a saturated aqueous solution of sodium chloride.

PREPARATION 1

3α-Benzoyloxy-5α-hydroxy-4-iodo-2β-methoxymethylcyclopentaneacetic Acid γ-Lactone (Formula VIII: $R_4$ is benzoyl)

Refer to Chart A. To a mixture of optically active laevorotatory (−) iodolactone VII (E. J. Corey et al, J. Am. Chem. Soc. Vol. 92, p. 397 (1970), 75 g.) in 135 ml. of dry pyridine under a nitrogen atmosphere is added 30.4 ml. of benzoyl chloride with cooling to maintain the temperature at about 20°–40° C. Stirring is continued for an additional 30 min. About 250 ml. of toluene is added and the mixture concentrated under reduced pressure. The residue is dissolved in one l. of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the title compound, m.p. 84°–86° C.; $[\alpha]_D+7°$ (CHCl$_3$); infrared spectral absorptions at 1768, 1722, 1600, 1570, 1490, 1275, 1265, 1180, 1125, 1090, 1060, 1030, and 710 cm$^{-1}$; and NMR (nuclear magnetic resonance) peaks at 2.1–3.45, 3.3, 3.58, 4.38, 5.12, 5.51, 7.18–7.58, and 7.83–8.05δ.

Following the procedures of Preparation 1, the optically active Formula-VII iodolactone is transformed to a Formula-VIII compound using, instead of benzoyl chloride, an $R_4Cl$ reactant wherein $R_4$ is substituted benzoyl, e.g. (2-, 3- or 4-)methylbenzoyl, (2-, 3-, or 4-)ethylbenzoyl, (2-, 3-, or 4-)-isopropylbenzoyl, (2-, 3-, or 4-)tertbutylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, 2-, 3-, or 4-phenethylbenzoyl, 2-, 3-, or 4-nitrobenzoyl, (2,4-, 2,5-, or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; monoesterified phthaloyl, e.g.

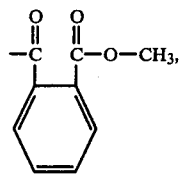

isophthaloyl, e.g.

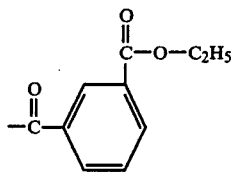

or terephthaloyl, e.g.

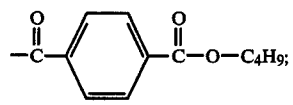

(1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5- or 8-)nitro-1-naphthoyl, 4,5-dinitro-1-naphthoyl, (3-, 4-, 6-, 7- or 8-(methyl-1-naphthoyl, 4-ethyl-2-naphthoyl, and (5- or 8-)nitro-2-naphthoyl; and acetyl.

Following the procedures of Preparation 1, but replacing that optically active Formula-VII iodolactone with the racemic compound of that formula and the mirror image thereof, and employing either benzoyl chloride or each of the $R_4Cl$ reactants disclosed above, there is obtained the corresponding racemic Formula-VIII compound.

PREPARATION 2

3α-Benzoyloxy-5α-hydroxy-2β-methoxymethylcyclopentaneacetic Acid γ-Lactone (Formula IX: $R_4$ is benzoyl)

Refer to Chart A. To a solution of the optically active Formula-VIII benzoxy compound (Preparation 1, 60 g.) in 240 ml. of dry benzene is added 2,2'-azobis-(2-methylpropionitrile) (approximately 60 mg.). The mixture is cooled to 15° C. and to it is added a solution of 75 g. tributyltin hydride in 600 ml. of ether, with stirring, at such a rate as to maintain continuous reaction at about 25° C. When the reaction is complete as shown by TLC (thin layer chromatography) the mixture is concentrated under reduced pressure to an oil. The oil is mixed with 600 ml. of Skellysolve B (isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product is separated, dried over magnesium sulfate, and concentrated under reduced pressure to an oil, 39 g. of the title compound. An analytical sample gives $[\alpha]_D - 99°$ ($CHCl_3$); infrared spectral absorptions at 1775, 1715, 1600, 1585, 1490, 1315, 1275, 1180, 1110, 1070, 1055, 1025, and 715 $cm^{-1}$; NMR peaks at 2.5–3.0, 3.25, 3.34, 4.84–5.17, 5.17–5.4, 7.1–7.5, and 7.8–8.05δ; and mass spectral peaks at 290, 168, 105, and 77.

Following the procedures of Preparation 2, each of the optically active or racemic Formula-VIII compounds following Preparation 1 is transformed to the corresponding optically active or racemic Formula-IX compound.

PREPARATION 3

3α-Benzoyloxy-5α-hydroxy-2β-hydroxymethylcyclopentaneacetic Acid γ-Lactone (Formula X: $R_4$ is benzoyl)

Refer to Chart A. To a cold (0°–5° C.) solution of lactone IX (Preparation 2, 20 g.) in 320 ml. of methylene chloride under nitrogen is added a solution of 24.8 ml. of boron tribromide in 320 ml. of dichloromethane, dropwise with vigorous stirring over a period of 50 min. at 0°–5° C. Stirring and cooling are continued for 1 hr. When the reaction is complete, as shown by TLC, there is cautiously added a solution of sodium carbonate (78 g. monohydrate) in 200 ml. of water. The mixture is stirred at 0°–5° C. for 10–15 min., saturated with sodium chloride, and the ethyl acetate layer separated. Additional ethyl acetate extractions of the water layer are combined with the main ethyl acetate solution. The combined solutions are rinsed with brine, dried over sodium sulfate and concentrated under reduced pressure to an oil, 18.1 g. of the title compound. An analytical sample has m.p. 116°–118° C.; $[\alpha]_D - 80°$ ($CHCl_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0δ.

Following the procedures of Preparation 3, each of the optically active or racemic Formula-IX compounds following Preparation 2 is transformed to the corresponding optically active or racemic Formula-X hydroxymethyl compound.

PREPARATION 4

3α-Benzoyloxy-2β-carboxaldehyde-5α-hydroxy-cyclopentaneacetic Acid γ-Lactone (Formula XI: $R_4$ is benzoyl)

Refer to Chart A. To a mixture of 150 ml. of dry dichloromethane and Collins' reagent (J. C. Collins et al, Tetrahedron Lett. 3363 (1968), 28 g.) at about 10° C. under nitrogen is added, with vigorous stirring, a cold (10° C.) solution of the optically active hydroxymethyl lactone X (Preparation 3, 5.0 g.) in 150 ml. of dichloromethane. After 5-min. additional stirring, about 100 ml. of dry benzene is added, the mixture is filtered, and the solution is concentrated under reduced pressure. The volume is brought to about 150 ml. with benzene. The solution of the Formula-XI title compound is used directly.

From a similar run, there is obtained by concentration of the benzene solution under reduced pressure an oil which, on trituration with ether, yields crystals of the optically active Formula-XI compound, m.p. 115° C. (dec.); and having NMR peaks at 1.8–3.7, 4.9–5.2, 5.54–5.77, 7.2–7.6, 7.7–8.0, and 9.8δ.

Following the procedures of Preparation 4, each of the optically active or racemic Formula-X hydroxymethyl compounds following Preparation 3 is transformed to the corresponding optically active or racemic Formula-XI aldehyde wherein $R_4$ is one of the $R_4$ groups listed after Preparation 1, e.g. 2-methylbenzoyl, pentamethylbenzoyl, 2,5-dinitrobenzoyl, monomethylphthaloyl, 1-naphthoyl, acetyl, and the like.

EXAMPLE 1

Dimethyl 2-Oxo-3-methylheptylphosphonate,

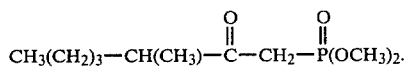

n-Butyllithium (150 ml.) is slowly added to a solution of dimethyl methylphosphonate (25.6 g.) in 475 ml. of tetrahydrofuran (THF) at about −65° C. To the mixture is added a solution of racemic ethyl 2-methylhexanoate (18.4 g.) in 50 ml. of THF, and the resulting mixture is stirred at −70° C. for 2 hrs. Then, 16 ml. of acetic acid is added, and the mixture is concentrated under reduced pressure. The residue is mixed with dichloromethane (about 400 ml.) and water (about 50 ml.), shaken, and separated. The organic phase is dried over magnesium sulfate and concentrated. Distillation yields the title compound, 16.7 g., b.p. 126°–129° C./1 mm.

Following the procedures of Example 1 but replacing racemic ethyl 2-methylhexanoate with the ethyl esters of the (+) and (−) isomers of 2-methylhexanoic acid (see P. A. Levene et al., J. Biol. Chem. 70, 211 (1926) and 84, 571 (1929)) there are obtained the corresponding optically active (+) and (−) title compounds.

Likewise following the procedures of Example 1, but replacing ethyl 2-methylhexanoate with optically active or racemic ethyl 2-ethylhexanoate, there are obtained the corresponding optically active or racemic phosphonates of the formula

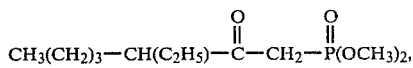

i.e. homologues of the title compound wherein the 3-methyl group is replaced by 3-ethyl.

EXAMPLE 2

3α-Benzoyloxy-5α-hydroxy-2β-(3-oxo-4-methyl-trans-1-octenyl)-1α-cyclopentaneacetic Acid γ-Lactone (Formula XII: $R_2$ is hydrogen, $R_3$ is methyl, and $R_4$ is benzoyl)

Refer to Chart A. A solution of racemic dimethyl 2-oxo-3-methylheptylphosphonate (Example 1, 7.9 g.) in 36 ml. of THF is added, with stirring, to a cold (5° C.) suspension of sodium hydride (55%, 1.62 g.) in 180 ml. of THF. Thereafter the reaction mixture is stirred at about 25° C. for 2.5 hrs., and cooled to −10° C. To the mixture is added a benzene solution of optically active aldehyde XI (Preparation 4, 108 ml.). After 1.5 hrs., 1.8 ml. of acetic acid is added and the THF distilled under vacuum. The residue is dissolved in ethyl acetate and the solution is washed with brine, dried over sodium sulfate, and concentrated under reduced pressure. Chromatography over silica gel using 25–30% ethyl acetate in Skellysolve B (isomeric hexanes) for elution yields the separated C-16 epimers of the Formula-XII title compound.

Following the procedures of Example 2, using the optically active aldehyde XI, but replacing the racemic phosphonate with each of the optically active (+) and (−) phosphonates following Example 1, there are obtained the corresponding optically active Formula-XII compounds.

Following the procedures of Example 2, but replacing the aldehyde XI with each of the optically active or racemic Formula-XI aldehydes disclosed following Preparation 4, and using either the optically active or racemic phosphonates of and following Example 1, there are obtained the corresponding Formula-XII compounds wherein $R_4$ corresponds to the $R_4$ moiety on the Formula-XI aldehyde. Thus, as in Example 2, the optically active Formula-XII aldehydes, when reacted with a racemic phosphonate, each yield a pair of diastereomers, i.e. 16-epimers of XII, which are separable by methods known to those skilled in the art, e.g. by silica gel chromatography. The optically active aldehydes, reacted with an optically active phosphonate, each yield the corresponding optically active compound XII. The racemic Formula-XI aldehydes, when reacted with a racemic phosphonate, each yield two pairs of Formula-XII racemates which are separable into separate pairs of racemic compounds by methods known in the art, e.g. silica gel chromatography. The racemic aldehydes, reacted with an optically active phosphonate, each yield a pair of diastereomers, which are separable, e.g. by silica gel chromatography.

Likewise following the procedures of Example 2, but replacing dimethyl 2-oxo-3-methylheptylphosphonate with optically active or racemic dimethyl 2-oxo-3-ethylheptylphosphonate described following Example 1, and reacting those phosphonates with the optically active or racemic Formula-XI aldehydes disclosed following Preparation 4, there are obtained the corresponding optically active or racemic Formula-XII compounds wherein $R_2$ is hydrogen, $R_3$ is ethyl, and $R_4$ is the same as that $R_4$ moiety on the intermediate aldehyde.

EXAMPLE 3

3α-Benzoyloxy-5α-hydroxy-2β-(3α-hydroxy-4-methyl-trans-1-octenyl)-1α-cyclopentane-acetic Acid γ-Lactone (Formula XIII: $R_2$ is hydrogen, $R_3$ is methyl, $R_4$ is benzoyl, and ∿∿∿ is alpha)

Refer to Chart A. A solution containing the 16-epimers of ketone XII (Example 2, 2.75 g.) in 14 ml. of 1,2-dimethoxyethane is added to a mixture of zinc borohydride prepared from zinc chloride (anhydrous, 4.94 g.) and sodium borohydride (1.12 g.) in 48 ml. of dry 1,2-dimethoxyethane, with stirring and cooling to −10° C. Stirring is continued for 2 hrs. at 0° C., and water (7.8 ml.) is cautiously added, followed by 52 ml. of ethyl acetate. The mixture is filtered, and the filtrate is separated. The ethyl acetate solution is washed with brine, dried over sodium sulfate, and concentrated under reduced pressure to a mixture of the corresponding Formula-XIII 15-alpha and 15-beta isomers. The compounds are subjected to chromatography on a silica gel column, eluting with ethyl acetate, to separate the 15-alpha (less polar) and 15-beta isomers of the C-16 epimers of the Formula-XIII title compounds.

Following the procedures of Example 3, the optically active or racemic Formula-XII ketones derived from the optically active or racemic phosphonates, as described following Example 2, wherein $R_4$ is benzoyl, are transformed to the corresponding optically active or racemic Formula-XIII hydroxy compounds.

Also following the procedures of Example 3, each of the optically active or racemic Formula-XII ketones described following Example 2 wherein $R_4$ is other than benzoyl is transformed to the corresponding Formula-XIII $3'\alpha$ and $3'\beta$ hydroxy compounds retaining the $R_4$ moiety of the Formula-XII ketone.

Likewise following the procedures of Example 3, each of the optically active or racemic 4'-ethyl Formula-XII ketones described following Example 2 is transformed to the corresponding 4'-ethyl Formula-XIII hydroxy compounds.

EXAMPLE 4

$3\alpha,5\alpha$-Dihydroxy-$2\beta$-($3\alpha$-hydroxy-4-methyl-trans-1-octenyl)-$1\alpha$-cyclopentaneacetic Acid γ-Lactone (Formula XIV: $R_2$ is hydrogen and $R_3$ is methyl)

Refer to Chart A. Potassium carbonate (0.79 g.) is added to a solution of the mixed C-16 alpha and beta epimeric alpha-hydroxy Formula-XIII compounds (Example 3, 2.2 g.) in 25 ml. of methanol, and the mixture is stirred for 1 hr. at about 25° C. Thereafter, 80 ml. of chloroform is added, the mixture is filtered, and the organic phase is concentrated under reduced pressure. The residue is taken up in dichloromethane and the solution washed with brine. Concentration of the organic phase gives a residue which is triturated with Skellysolve B, then concentrated to the corresponding mixed C-16 alpha and beta epimeric 15-alpha Formula-XIV title compounds, 1.2 g.

Following the procedures of Example 4, each of the optically active or racemic Formula-XIII hydroxy compounds described following Example 3, wherein $R_4$ is benzoyl, is transformed to the corresponding optically active or racemic Formula-XIV title compound.

Also following the procedures of Example 4, but replacing those Formula-XIII compounds with each of the optically active or racemic Formula-XIII compounds disclosed following Example 3, wherein $R_4$ is other than benzoyl, the said compounds are transformed to the corresponding optically active or racemic Formula-XIV title compounds.

Likewise following the procedures of Example 4, but employing the 4'-ethyl Formula-XIII hydroxy compounds, i.e. wherein $R_3$ is ethyl, there are obtained the corresponding optically active or racemic Formula XIV title compounds wherein $R_2$ is hydrogen and $R_3$ is ethyl.

EXAMPLE 5

$3\alpha,5\alpha$-Dihydroxy-$2\beta$-($3\alpha$-hydroxy-4-methyl-trans-1-octenyl)-$1\alpha$-cyclopentaneacetic Acid γ-Lactone, 3,3'-Bis(tetrahydropyranyl) Ether (Formula XV: $R_2$ is hydrogen and $R_3$ is methyl)

Refer to Chart B. A solution of the Formula-XIV diols (Example 4, 1.3 g.), 4.25 ml. of dihydropyran, and 0.019 g. of p-toluenesulfonic acid in 35 ml. of dichloromethane is stirred at about 25° C. for 30 min. The solution is washed with potassium bicarbonate solution, dried, and concentrated under reduced pressure to yield the Formula-XV title compounds, 2.7 g.

Following the procedures of Example 5, each of the optically active or racemic Formula-XIV compounds described following Example 4 is transformed to the corresponding optically active or racemic Formula-XV compound, e.g. those wherein $R_2$ is hydrogen and $R_3$ is either methyl or ethyl.

EXAMPLE 6

$3\alpha,5\alpha$-Dihydroxy-$2\beta$-($3\alpha$-hydroxy-4-methyltrans-1-octenyl)-$1\alpha$-cyclopentaneacetaldehyde γ-Lactol, 4,3'-Bis(tetrahydropyranyl) Ether (Formula XVI: $R_2$ is hydrogen, $R_3$ is methyl, and ∿∿ is alpha or beta)

Refer to Chart B. Diisobutylaluminum hydride (2.6 ml.) in 25 ml. of toluene is added dropwise to a stirred solution of the Formula-XV tetrahydropyranyl ethers (Example 5, 2.7 g.) in 30 ml. of toluene cooled to $-70°$ C. Stirring is continued at $-70°$ C. for 30 min., whereupon a solution of 12 ml. of THF and 6 ml. of water is cautiously added. The mixture is filtered and the filtrate is washed with brine, dried, and concentrated to the mixed alpha and beta hydroxy isomers of the Formula-XVI title compounds, 2.4 g., showing no lactone absorption in their infrared spectra.

Following the procedures of Example 6, each of the optically active or racemic Formula-XV compounds described following Example 5 is transformed to the corresponding optically active or racemic Formula-XVI compound.

EXAMPLE 7

16-Methyl-PGF$_{2\alpha}$11,15-Bis(tetrahydropyranyl) Ether (Formula XVII: $R_2$ and $R_7$ are hydrogen, and $R_3$ is methyl)

Refer to Chart B. 4-Carboxybutyl triphenylphosphonium bromide (5.94 g.) is added to a solution of sodio dimethylsulfinylcarbanide prepared from sodium hydride (60%. 0.90 g.) and 19 ml. of dimethylsulfoxide (DMSO) and the mixture is stirred for 20 min. at about 25° C. To this reagent is added dropwise the Formula-XVI lactols (Example 6, 2.4 g.) in 4 ml. of DMSO. The mixture is stirred at about 25° C. for 16 hrs., then diluted with about 30 ml. of benzene. To it is added dropwise a solution of potassium hydrogen sulfate (3.64 g.) in 30 ml. of water, with cooling and stirring. The organic layer is separated, washed with water, dried, and concentrated under reduced pressure. The residue is chromatographed over silica gel using chloroform-methanol (10:1) for elution, to yield the Formula-XVII compounds, 1.5 g.

Following the procedures of Example 7, each of the optically active or racemic Formula-XVI compounds described following Example 6 is transformed to the corresponding optically active or racemic Formula-XVII compound.

Likewise following the procedures of Example 7, but replacing 4-carboxybutyl triphenylphosphonium bromide with other compounds of the formula Br(C$_6$H$_5$)$_3$P(CH$_2$)$_4$COOR$_7$, wherein $R_7$ is not only hydrogen but also alkyl of one to 8 carbon atoms, inclusive, as defined herein, there are obtained the corresponding Formula-XVII compounds wherein $R_7$ is alkyl of one to 8 carbon atoms, inclusive.

EXAMPLE 8

16-Methyl-PGF$_{2\alpha}$ (Formula III: R$_2$ and R$_7$ are hydrogen, and R$_3$ is methyl)

Refer to Cart B. To a solution of the Formula-XVII bis(tetrahydropyranyl) ethers (Example 7, 0.6 g.) in 5 ml. of THF is added 15.5 ml. of 67% (aqueous) acetic acid. The mixture is warmed to about 55° for 2 hrs., then concentrated under 1 mm. pressure. The residue is dissolved in benzene and chromatographed over silica gel using chloroform-methanol (4:1) for elution. Those fractions shown by thin-layer chromatography (TLC) using the A-IX' system to contain the desired product are combined and concentrated to yield the Formula-III title compounds, 0.23 g. High-resolution mass spectrum of trimethylsilyl (TMS) derivative: M+, 656.4135.

Following the procedures of Example 8, each of the optically active or racemic Formula-XVII compounds described following Example 7 is transformed to the corresponding optically active or racemic Formula-III compound. Thus, there are obtained also the corresponding 16-ethyl-PGF$_{2\alpha}$ compounds.

EXAMPLE 9

16-Methyl-PGE$_2$, 11,15-Bis(tetrahydropyranyl)

Ether (Formula XVIII: R$_2$ and R$_7$ are hydrogen, and R$_3$ is methyl)

Refer to Chart B. To a solution of the Formula-XVII bis(tetrahydropyranyl) ether of 16-methyl-PGF$_{2\alpha}$ (Example 7, 0.9 g.) in 13 ml. of acetone at −20° C. is added dropwise 1.0 ml. of Jones reagent (2.1 g. of chromic anhydride, 6 ml. of water, and 1.7 ml. of concentrated sulfuric acid). After 15 min. stirring, 1 ml. of 2-propanol is added, with additional stirring, followed by 35 ml. of water. The solution is shaken with three portions of dichloromethane, the organic extracts are combined, dried, and concentrated under reduced pressure. The residue is chromatographed over silica gel to yield a fraction shown by TLC to contain the Formula-XVIII title compounds, 0.5 g.

Following the procedures of Example 9, each of the optically active or racemic Formula-XVII compounds described following Example 7 is transformed to the corresponding optically active or racemic Formula-XVIII compound. There is thus obtained, for example, the 11,15-bis(tetrahydropyranyl) ether of 16-methyl-PGE$_2$, methyl ester, i.e. Formula XVIII wherein R$_2$ is hydrogen, and R$_3$ and R$_7$ are methyl. Likewise, there is obtained the 11,15-bis-(tetrahydropyranyl) ether of 16-ethyl-PGE$_2$, i.e. Formula XVIII wherein R$_2$ and R$_7$ are hydrogen, and R$_3$ is ethyl.

EXAMPLE 10

16Methyl-PGE$_2$ (Formula II: R$_2$ and R$_7$ are hydrogen, and R$_3$ is methyl)

Refer to Chart B. A solution prepared from the Formula-XVIII diether (Example 9, 0.5 g.) in 2 ml. of THF and 20 ml. of 67% (aqueous) acetic acid is maintained at 40° C. for 2 hrs. The solvent is removed under reduced pressure, and the residue is chromatographed over silica gel using chloroform-methanol (10:1) for elution. The fractions containing the desired product as shown by TLC are combined and concentrated to yield the Formula-II title compounds, 0.17 g. High-resolution mass spectrum of TMS derivative: M+-C$_6$H$_{13}$, 497.2582.

Following the procedures of Example 10, each of the optically active or racemic Formula-XVIII compounds described following Example 9 is transformed to the corresponding optically active or racemic Formula-II compounds. There is thus obtained, for example, 16-methyl-PGE$_2$, methyl ester, i.e. Formula II wherein R$_2$ is hydrogen, and R$_3$ and R$_7$ are methyl. Likewise, there is obtained 16-ethyl PGE$_2$, i.e. Formula II wherein R$_2$ and R$_7$ are hydrogen, and R$_3$ is ethyl.

EXAMPLE 11

Dimethyl 2-Oxo-3,3-dimethylheptylphosphonate,

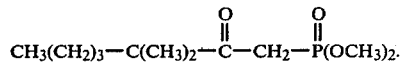

n-Butyllithium (400 ml.) is slowly added to a solution of dimethyl methylphosphonate (73.7 g.) in 1.3 l. of THF at about −66° C. To the mixture is added a solution of ethyl 2,2-dimethylhexanoate (53 g.) in 150 ml. of THF, and the resulting mixture is stirred at −70° C. for 2 hrs. Then, 46 ml. of acetic acid is added, and the mixture is concentrated under reduced pressure. The residue is mixed with portions of dichloromethane (about 1.2 l.) and water (about 150 ml.), shaken, and separated. The organic phase is dried over magnesium sulfate and concentrated. Distillation yields the title compound, 41.6 g., b.p. 117°-120° C./1 mm.

Following the procedures of Example 11, but replacing ethyl 2,2-dimethylhexanoate with ethyl 2,2-diethylhexanoate or ethyl 2-ethyl-2-methylhexanoate, there are obtained the corresponding phosphonates, i.e. dimethyl 2-oxo-3,3-diethylheptylphosphonate and dimethyl 2-oxo-3-methyl-3-ethylheptylphosphonate.

EXAMPLE 12

3α-Benzoyloxy-5α-hydroxy-2β(3-oxo-4,4-dimethyl-trans-1-octenyl)-1α-cyclopentaneacetic Acid γ-Lactone (Formula XII: R$_2$ and R$_3$ are methyl, and R$_4$ is benzoyl)

Refer to Chart A. A solution of dimethyl 2-oxo-3,3-dimethylheptylphosphonate (Example 11, 11.0 g.) in 50 ml. of THF is added to a cold (5° C.) suspension of sodium hydride (55%, 2.26 g.) in 250 ml. of THF, with stirring. Thereafter the reaction mixture is stirred at about 25° C. for 2.5 hrs., and cooled to −10° C. To the mixture is added a benzene solution of optically active aldehyde XI (Preparation 4, 150 ml.). After 1.5 hrs., 2 ml. of acetic acid is added and the THF distilled under vacuum. The residue is dissolved in ethyl acetate and the solution is washed with brine, dried over sodium sulfate, and concentrated under reduced pressure. Chromatography over silica gel using 25-30% ethyl acetate in Skellysolve B for elution yields the corresponding optically active title compound, 4.6 g, m.p. 82°-3° C.

Following the procedures of Example 12, but replacing the aldehyde XI with each of the optically active or racemic Formula XI aldehydes disclosed following Preparation 4 there is obtained the corresponding optically active or racemic Formula-XII compound wherein R$_4$ corresponds to the R$_4$ moiety on the Formula-XI aldehyde.

Likewise following the procedures of Example 12, but replacing dimethyl 2-oxo-3,3-dimethylheptylphosphonate with dimethyl 2-oxo-3-diethylheptylphosphonate or dimethyl 2-oxo-3-ethyl-3-methylheptylphosphonate described following Example 11, there is obtained

EXAMPLE 13

3α-Benzoyloxy-5α-hydroxy-2β(3-hydroxy-4,4-dimethyl-trans-1-octenyl)-1α-cyclopentaneacetic Acid γ-Lactone (Formula XIII: $R_2$ and $R_3$ are methyl, $R_4$ is benzoyl, and ∿ is alpha or beta)

Refer to Chart A. A solution of ketone XII (Example 12, 4.65 g.) in 30 ml. of 1,2-dimethoxyethane is added to a mixture of zinc borohydride prepared from zinc chloride (anhydrous, 7.95 g.) and sodium borohydride (1.75 g.) in 71 ml. of dry 1,2-dimethoxyethane, with stirring and cooling to $-10°$ C. Stirring is continued for 2 hrs. at 0° C., and water (12 ml.) is cautiously added, followed by 25 ml. of ethyl acetate. The mixture is filtered, and the filtrate is separated. The ethyl acetate solution is washed with brine, dried over sodium sulfate, and concentrated under reduced pressure to a mixture of the Formula-XIII isomers. The alpha and beta isomeric title compounds are separated by chromatography on a silica gel column, eluting with ethyl acetate, to yield 2.1 g. of the alpha isomer and 0.4 g. of the beta isomer, respectively, of the optically active title compounds.

Following the procedures of Example 13, each of the optically active or racemic Formula-XII ketones disclosed following Example 12 is transformed to the corresponding Formula-XIII hydroxy compounds retaining the $R_4$ moiety of the Formula-XII ketone. Thus there are obtained Formula-XIII hydroxy compounds wherein $R_2$ and $R_3$ are both methyl or are both ethyl, or wherein one is ethyl and the other is methyl.

EXAMPLE 14

3α,5α-Dihydroxy-2β-(3α-hydroxy-4,4-dimethyltrans-1-octenyl)-1α-cyclopentaneacetic Acid γ-Lactone (Formula XIV: $R_2$ and $R_3$ are methyl)

Refer to Chart A. Potassium carbonate (0.72 g.) is added to a solution of the optically active alpha-hydroxy Formula-XIII compound (Example 13, 2.1 g.) in 35 ml. of methanol, and the mixture is stirred for 1 hr. at about 25° C. Thereafter, 75 ml. of chloroform is added, the mixture is filtered, and the organic phase is concentrated under reduced pressure. The residue is taken up in dichloromethane and the solution washed with brine. Concentration of the organic phase gives a residue which is triturated with Skellysolve B, then concentrated to the corresponding optically active Formula-XIV title compound, 1.4 g.

Following the procedures of Example 14, but replacing the Formula-XIII compound with each of the optically active or racemic Formula-XIII compounds described following Example 3, having $R_4$ other than benzoyl, there is also obtained the corresponding optically active or racemic Formula-XIV title compound. Thus, there are obtained Formula-IV compounds wherein $R_2$ and $R_3$ are both methyl or are both ethyl, or wherein one is ethyl and the other is methyl.

EXAMPLE 15

3α,5α-Dihydroxy-2β-(3α-hydroxy-4,4-dimethyltrans-1-octenyl)-1α-cyclopentaneacetic Acid γ-Lactone, 3,3'(tetrahydropyranyl) Ether (Formula XV: $R_2$ and $R_3$ are methyl).

Refer to Chart B. A solution of the optically active Formula-XIV diol (Example 14, 1.4 g.), 4.3 ml. of dihydropyran, and 0.023 g. of p-toluenesulfonic acid in 30 ml. of dichloromethane is stirred at about 25° C. for 30 min. The solution is washed with potassium bicarbonate solution, dried, and concentrated under reduced pressure to yield the corresponding optically active Formula-XV title compound, 3.0 g.

Following the procedures of Example 15, the optically active or racemic Formula-XIV compounds described following Example 14 are transformed to the corresponding optically active or racemic Formula-XV compounds. Thus, there are obtained Formula-XV compounds wherein $R_2$ and $R_3$ are both methyl or are both ethyl, and wherein one is ethyl and the other is methyl.

EXAMPLE 16

3α,5α-Dihydroxy-2β-(3α-hydroxy-4,4-dimethyl-trans-1-octenyl)-1α-cyclopentaneacetaldehyde γ-Lactol, 3,3'-Bis(tetrahydropyranyl) Ether (Formula XVI: $R_2$ and $R_3$ are methyl, and ∿ is alpha or beta)

Refer to Chart B. Diisobutylaluminum hydride (2.5 ml.) in 16 ml. of toluene is added dropwise to a stirred solution of the optically active Formula-XV tetrahydropyranyl ether (Example 15, 3.0 g.) in 25 ml. of toluene cooled to $-70°$ C. Stirring is continued at $-70°$ C. for 30 min., whereupon a solution of 9 ml. of THF and 4.6 ml. of water is cautiously added. The mixture is filtered and the filtrate is washed with brine, dried, and concentrated to the mixed alpha and beta hydroxy isomers of the corresponding optically active Formula-XVI title compound, 2.8 g., showing no lactone absorption in its infrared spectrum.

Following the procedures of Example 16, the optically active or racemic Formula-XV compounds described following Example 15 are transformed to the corresponding optically active or racemic Formula-XVI compounds.

EXAMPLE 17

16,16-Dimethyl-PGF$_{2\alpha}$, 11,15-Bis(tetrahydropyranyl) Ether (Formula XVII: $R_2$ and $R_3$ are methyl, and $R_7$ is hydrogen)

Refer to Chart B. 4-Carboxybutyl triphenylphosphonium bromide (10.5 g.) is added to a solution of sodio dimethylsulfinylcarbanide prepared from sodium hydride (60%, 2.0 g.) and 50 ml. of DMSO, and the mixture is stirred for 20 min. at about 25° C. To this reagent is added dropwise the optically active Formula-XVI lactol (Example 16, 2.8 g.) in 9 ml. of DMSO. The mixture is stirred at about 25° C. for 2 hrs., then diluted with about 30 ml. of benzene. To it is added dropwise a solution of potassium hydrogen sulfate (6.4 g.) in 30 ml. of water, with cooling and stirring. The organic layer is separated, washed with water, dried, and concentrated under reduced pressure. The residue is chromatographed over silica gel using chloroform-methanol (10:1) for elution, to yield the corresponding optically active Formula-XVII compound, 1.6 g.

Following the procedures of Example 17, the optically active or racemic Formula-XVI compounds described following Example 16 are transformed to the corresponding optically active or racemic Formula-XVII compounds.

Likewise following the procedures of Example 17, but replacing 4-carboxybutyl triphenylphosphonium bromide with other compounds of the formula Br(C$_6$H$_5$)$_3$P(CH$_2$)$_4$COOR$_7$, wherein $R_7$ is not only hydrogen but also alkyl of one to 8 carbon atoms, inclusive, as defined herein, there are obtained the corresponding Formula-XVII compounds wherein $R_7$ is alkyl of one to 8 carbon atoms, inclusive.

EXAMPLE 18

16,16-Dimethyl-PGF$_{2\alpha}$ (Formula III: $R_2$ and $R_3$ are methyl, and $R_7$ is hydrogen)

Refer to Chart B. To a solution of the optically active Formula-XVII bis(tetrahydropyranyl) ether (Example 17, 0.8 g.) in 5.6 ml. of THF is added 18.6 ml. of 67% (aqueous) acetic acid. The mixture is warmed to about 55° for 2 hrs., then concentrated under 1 mm. pressure. The residue is dissolved in benzene and chromatographed over silica gel using chloroform-methanol (4:1) for elution. Those fractions shown by thin-layer chromatography (TLC) to contain the desired product are combined and concentrated to yield the corresponding optically active Formula-III title compound, 0.34 g. High-resolution mass spectrum of trimethylsilyl (TMS) derivative: $M^+-CH_3$, 655.4047.

Following the procedures of Example 18, the optically active or racemic Formula-XVII compounds described following Example 17 are transformed to the corresponding optically active or racemic Formula-III compounds. Thus, there are also obtained the corresponding 16,16-diethyl- and 16-ethyl-16-methyl-PGF$_{2\alpha}$ compounds.

EXAMPLE 19

16,16-Dimethyl-PGE$_2$, 11,15-Bis(tetrahydropyranyl) Ether (Formula XVIII: $R_2$ and $R_3$ are methyl, and $R_7$ is hydrogen)

Refer to Chart B. To a solution of the optically active Formula-XVII bis(tetrahydropyranyl) ether of 16,16-dimethyl-PGF$_{2\alpha}$ (Example 17, 0.8 g.) in 13 ml. of acetone at $-20°$ C. is added dropwise 0.88 ml. of Jones reagent (2.1 g. of chromic anhydride, 6 ml. of water, and 1.7 ml. of concentrated sulfuric acid). After 15 min. stirring, 1 ml. of 2-propanol is added, with additional stirring followed by 35 ml. of water. The solution is shaken with three portions of dichloromethane, the organic extracts are combined, dried, and concentrated under reduced pressure. The residue is chromatographed over silica gel to yield a fraction shown by TLC to contain the corresponding optically active Formula-XVIII title compound, 0.7 g.

Following the procedures of Example 19, the optically active or racemic Formula-XVII compounds described following Example 18 are transformed to the corresponding optically active or racemic Formula-XVIII compounds. There are thereby obtained the 16,16-diethyl and 16-ethyl-16-methyl PGE$_2$ derivatives of Formula XVIII wherein $R_2$ and $R_3$ are both methyl or both ethyl, or wherein one is ethyl and the other is methyl.

EXAMPLE 20

16,16-Dimethyl-PGE$_2$ (Formula II: $R_2$ and $R_3$ are methyl, and $R_7$ is hydrogen)

Refer to Chart B. A solution prepared from the optically active Formula-XVIII diether (Example 19, 0.7 g.) in 5 ml. of THF and 18 ml. of 67% (aqueous) acetic acid is maintained at 40° C. for 2 hrs. The solvent is removed under reduced pressure, and the residue is chromatographed over silica gel using chloroform-methanol (10:1) for elution. The fractions containing the desired product as shown by TLC are combined and concentrated to yield the optically active Formula-II title compound, 0.37 g. High-resolution mass spectrum of TMS derivative: $M^+-C_7H_{15}$, 497.2521.

Following the procedures of Example 20, the optically active or racemic Formula-XVIII compounds described following Example 19 are transformed to the corresponding optically active or racemic Formula-II compounds. Thus, there are obtained the corresponding 16,16-diethyl-PGE$_2$ and 16-ethyl-16-methyl-PGF$_{2\alpha}$ compounds.

EXAMPLE 21

16-Methyl-PGF$_{2\alpha}$ and 16-Methyl-PGF$_{2\beta}$ (Formulas III and IV, respectively: $R_1$ and $R_2$ are hydrogen, and $R_3$ is methyl)

Refer to Chart C. A solution of 16-methyl-PGE$_2$ (Example 10, 300 mg.), 20 ml. of tetrahydrofuran, 2.0 ml. of hexamethyldisilazane, and 0.15 ml. of trimethylsilyl chloride is stirred at 25° for 20 hrs. The reaction mixture is concentrated in vacuo, diluted with benzene, and concentrated, and this procedure is repeated. The residue is dissolved in 10 ml. of methanol, cooled in an ice-methanol bath, and to it is added sodium borohydride (60 mg.) in 20 ml. of cold water dropwise. The methanol is removed, and aqueous phase is extracted with dichloromethane, and the resulting dichloromethane solution is dried and concentrated in vacuo. The residue is chromatographed on 45 g. of silica gel using 70 ml. of ethyl acetate and then a gradient of 0–8% methanol ethyl acetate as eluting solvent, collecting 10-ml. fractions. Fractions shown by TLC to contain the Formula-III title compound, free of starting materials and by-products, are combined and concentrated to yield the desired Formula-III PGF$_{2\alpha}$-type title compound. Similarly, fractions shown to contain the Formula-IV title compound are combined and concentrated to yield the desired Formula-IV PGF$_{2\beta}$-type title compound.

Following the procedure of Example 21, 16,16-dimethyl-PGE$_2$ (Example 20) is transformed to 16,16-dimethyl-PGF$_{2\alpha}$ and -PGF$_{2\beta}$.

Following the procedures of Example 21, each of the optically active or racemic Formula-II PGE$_2$-type compounds described following Examples 10 and 20 is transformed to the corresponding optically active or racemic Formula-III PGF$_{2\alpha}$-type and Formula-IV PGF$_{2\beta}$-type compounds. Thus, there are obtained the optically active or racemic 16-ethyl-, 16,16-diethyl- and 16-ethyl-16-methyl-PGF$_{2\alpha}$ and -PGF$_{2\beta}$ type compounds.

EXAMPLE 22

16-Methyl-PGA$_2$ (Formula V: $R_1$ and $R_2$ are hydrogen, and $R_3$ is methyl)

Refer to Chart C. A solution of 16-methyl-PGE$_2$ (Example 10, 300 mg.), 4 ml. of tetrahydrofuran and 4 ml. of 0.5 N hydrochloric acid is left standing at 25° for five days. Brine and dichloromethane-ether (1:3) are added and the mixture is stirred. The organic layer is separated, dried and concentrated. The residue is dissolved in ether which is washed with saturated aqueous sodium bicarbonate, dried and concentrated. The aqueous phase is quickly acidified with hydrochloric acid and extracted with dichloromethane which in turn is dried and concentrated. The residue is again dissolved in ether, extracted with aqueous sodium bicarbonate, and the aqueous phase is worked up as reported above. This procedure is repeated one additional time to yield the desired Formula-V title compound.

Following the procedure of Example 22, 16,16-dimethyl-PGE$_2$ (Example 20) is transformed to 16,16-dimethyl-PGA$_2$.

Following the procedures of Example 22, each of the optically active or racemic Formula-II PGE$_2$-type compounds described following Examples 10 and 20 is transformed to the corresponding optically active or racemic Formula-V PGA$_2$-type compound. Thus, there are obtained the optically active or racemic 16-ethyl-, 16,16-diethyl-, and 16-ethyl-16-methyl-PGA$_2$ type compounds.

EXAMPLE 23

16-Methyl-PGA$_2$, Methyl Ester (Formula V: R$_1$ and R$_3$ are methyl, and R$_2$ is hydrogen)

A mixture of 16-methyl-PGE$_2$, methyl ester, (following Example 10, 6 mg.), dicyclohexylcarbodiimide (20 mg.), copper (II) chloride dihydrate (2 mg.), and diethyl ether (2 ml.) is stirred under nitrogen at 25° C. for 16 hrs. Then, additional dicyclohexylcarbodiimide (20 mg.) is added, and the mixture is stirred an additional 32 hrs. at 25° C. under nitrogen. The resulting mixture is filtered, and the filtrate is evaporated under reduced pressure. The residue is chromatographed by preparative TLC with the A-IX system to give the desired Formula-V product.

Following the procedure of Example 23, but substituting for the 16-methyl PGE$_2$ compound, the methyl ester of 16,16-dimethyl-PGE$_2$, there is obtained the corresponding Formula-V compound, viz., the methyl ester of 16,16-dimethyl-PGA$_2$.

Also following the procedure of Example 23, but substituting for the 16-methyl-PGE$_2$ compound, the PGE$_2$ compounds of and following Examples 10 and 20, there are obtained the corresponding Formula-V PGA$_2$-type compounds.

EXAMPLE 24

16-Methyl-PGB$_2$ (Formula VI: R$_1$ and R$_2$ are hydrogen, and R$_3$ is methyl)

Refer to Chart C. A solution of 16-methyl-PGE$_2$ (Example 10, 200 mg.) in 100 ml. of 50% aqueous ethanol containing about one gram of potassium hydroxide is kept at 25° C. for 10 hrs. under nitrogen. Then, the solution is cooled to 10° C. and neutralized by addition of 3 N. hydrochloric acid at 10° C. The resulting solution is extracted repeatedly with ethyl acetate, and the combined ethyl acetate extracts are washed with water and then with brine, dried, and evaporated to give the desired Formula-VI title compound.

Following the procedure of Example 24, 16-methyl-PGA$_2$ is also transformed to the PGB$_1$-type title compound.

Following the procedure of Example 24, 16,16-dimethyl-PGE$_2$ and 16,16-dimethyl-PGA$_2$ are transformed to 16,16-dimethyl-PGB$_2$.

Following the procedures of Example 24, each of the optically active or racemic Formula-II PGE$_2$-type compounds described following Examples 10 and 20, and each of the optically active or racemic Formula-V-PGA$_2$-type compounds described following Example 22 is transformed to the corresponding optically active or racemic Formula-VI PGB$_2$-type compound. Thus, there are obtained the optically active or racemic 16-ethyl-, 16,16-diethyl-, and 16-ethyl-16-methyl-PGB$_2$ type compounds.

EXAMPLE 25

16-Methyl-PGA$_2$ Methyl Ester (Formula V: R$_1$ and R$_3$ are methyl, and R$_2$ is hydrogen)

A solution of diazomethane (about 50% excess) in diethyl ether (25 ml.) is added to a solution of 16-methyl-PGA$_2$ (Example 22, 50 mg.) in 25 ml. of a mixture of methanol and ethyl ether (1:1). The mixture is allowed to stand at 25° C. for 5 min. Then, the mixture is evaporated to give the Formula-V title compound.

Following the procedure of Example 25, each of the other specific 16-methyl or 16,16-dimethyl-substituted PGB$_2$-type, PGA$_2$-type, PGE$_2$-type, and PGF$_2$-type free acids defined above is converted to the corresponding methyl ester.

Also following the procedure of Example 25, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 16-methyl-PGA$_2$. In the same manner, each of the other specific 16-methyl- or 16,16-dimethyl-substituted PGB$_2$-type, PGA$_2$-type, PGE$_2$-type, and PGF$_2$-type free acids defined above is converted to the corresponding ethyl, butyl, 2-ethylhexyl, and cyclohexyl esters.

EXAMPLE 26

16-Methyl-PGE$_2$ Sodium Salt

A solution of 16-methyl-PGE$_2$ (Example 10, 100 mg.) in 50 ml. of a water-ethanol mixture (1:1) is cooled to 5° C. and neutralized with an equivalent amount of 0.1 N. aqueous sodium hydroxide solution. The neutral solution is evaporated to give the title compound.

Following the procedure of Example 26 but using potassium hydroxide, calcium hydroxide, tetramethylammonium hydroxide, and benzyltrimethylammonium hydroxide in place of sodium hydroxide, there are obtained the corresponding salts of 16-methyl-PGE$_2$.

Also following the procedure of Example 26 each of the 16-methyl or 16,16-dimethyl-substituted PGE$_2$-type, PGF$_2$-type, PGA$_2$-type, and PGB$_2$-type acids defined above is transformed to the sodium, potassium, calcium, tetramethylammonium, and benzyltrimethylammonium salts.

Following the procedures of Example 2, each of the pairs of diastereomers, i.e. C-16 epimers, of and following Examples 2 through 10, inclusive, are separated by methods known in the art, e.g. by silica gel chromatography. Those products shown to have the greatest biological activity by biological screening tests, e.g. smooth muscle strip tests and antisecretory in vivo tests referenced above, are the most useful for the purposes described herein.

The solvent systems used in thin layer chromatography herein include:
A IX Ethyl acetate-acetic acid-2,2,4-trimethylpentane-water (90:20:50:100).
A IX' Ethyl acetate-acetic acid-Skellysolve B (isomeric hexanes)-water (90:20:50:100).
See M. Hamberg and B. Samuelsson, J. Biol. Chem. 241, 257 (1966).

I claim:
1. An optically active compound of the formula

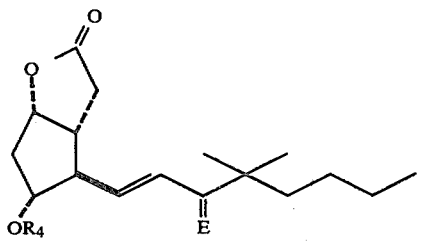

or a racemic compound of that formula and the mirror image thereof,
  wherein E is O=,
or

;

and
  wherein R₄ is

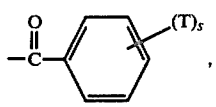 (1)

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms;

 (2)

wherein R₆ is alkyl of one to 4 carbon atoms, inclusive;

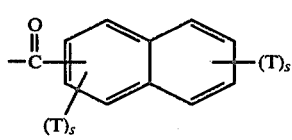 (3)

wherein T and s are as defined above; or
  (4) acetyl.

2. An optically active or racemic compound according to claim 1 wherein E is O=.
3. An optically active or racemic compound according to claim 2 wherein R₄ is benzoyl.
4. An optically active or racemic compound according to claim 1 wherein E is

5. An optically active or racemic compound according to claim 4 wherein R₄ is benzoyl.
6. An optically active compound of the formula

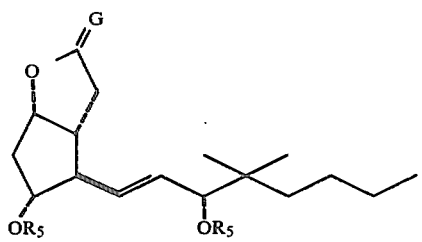

or a racemic compound of that formula and the mirror image thereof,
  wherein G is O=

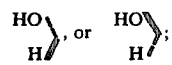

and
  wherein R₅ is hydrogen or tetrahydropyranyl.
7. An optically active or racemic compound according to claim 6 wherein G is O=.
8. An optically active or racemic compound according to claim 7 wherein R₅ is hydrogen.
9. An optically active or racemic compound according to claim 7 wherein R₅ is tetrahydropyranyl.
10. An optically active or racemic compound according to claim 6 wherein G is

.

11. An optically active or racemic compound according to claim 10 wherein R₅ is hydrogen.
12. An optically active or racemic compound according to claim 10 wherein R₅ is tetrahydropyranyl.
13. An optically active or racemic compound according to claim 6 wherein G is

.

14. An optically active or racemic compound according to claim 13 wherein R₅ is hydrogen.
15. An optically active or racemic compound according to claim 13 wherein R₅ is tetrahydropyranyl.

* * * * *

UNITED STATES PATENT OFFICE
CERTIFICATE OF CORRECTION

Patent No. 4,212,811          Dated 15 July 1980

Inventor(s) Barney J. Magerlein

It is certified that error appears in the above-identified patent and that said Letters Patent are hereby corrected as shown below:
Column 3, line 22, "wherein   indicates" should read -- wherein ∿ indicates --; lines 42-48,

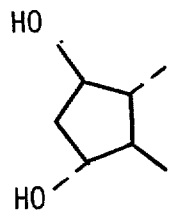   should read   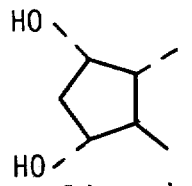   ;

Column 6, line 5, "to reduce the control" should read -- to reduce or control --;
Column 7, line 38 and 39, "approvimately" should read -- approximately --
Column 9, line 6, "concontrast" should read -- contrast --; line 43, "ester by alkyl" should read -- ester be alkyl --;
Column 13, lines 2-10, that portion of formula XVI reading

   should read   

UNITED STATES PATENT OFFICE
CERTIFICATE OF CORRECTION

Patent No. 4,212,811   Dated  15 July 1980

Inventor(s)  Barney J. Magerlein

It is certified that error appears in the above-identified patent and that said Letters Patent are hereby corrected as shown below:

Column 15, line 14, "wherein $R_2$, $R_3$, $R_7$, and     are as defined" should read -- wherein $R_2$, $R_3$, $R_7$, and $\sim$ are as defined --.

Signed and Sealed this

Twenty-ninth Day of September 1981

[SEAL]

Attest:

Attesting Officer

GERALD J. MOSSINGHOFF

Commissioner of Patents and Trademarks